United States Patent [19]

Des Garets

[11] Patent Number: 5,154,919
[45] Date of Patent: Oct. 13, 1992

[54] DEPILATORY COMPOSITION

[76] Inventor: Christian Des Garets, 9, rue Saint Florentin, 75008 Paris, France

[21] Appl. No.: 779,135

[22] Filed: Oct. 17, 1991

Related U.S. Application Data

[63] Continuation of Ser. No. 348,621, filed as PCT/FR88/00328, Jun. 21, 1988, abandoned.

[30] Foreign Application Priority Data

Jul. 6, 1987 [FR] France .................. 87 09552

[51] Int. Cl.⁵ .................................. A61K 7/15
[52] U.S. Cl. ............................. 424/73; 514/847; 514/880; 523/105
[58] Field of Search ............ 8/160, 161; 424/73; 514/843, 847, 880; 523/105

[56] References Cited

U.S. PATENT DOCUMENTS

| | | | |
|---|---|---|---|
| 2,091,313 | 7/1934 | Grant | 8/160 |
| 3,384,548 | 5/1968 | Zviak | 8/160 |
| 4,282,877 | 8/1981 | Mathews | 606/134 |
| 4,370,315 | 1/1983 | Greff | 424/73 |
| 4,631,064 | 12/1986 | Juneja | 8/160 |
| 4,830,633 | 5/1989 | Hori | 8/161 |
| 4,832,949 | 5/1989 | Royal | 424/73 |
| 4,842,610 | 6/1989 | Gordon | 8/160 |

FOREIGN PATENT DOCUMENTS 1185186 7/1984 Canada .

OTHER PUBLICATIONS

Chemical Abstracts, vol. 104, 1986, p. 377, resume No. 74822g, Columbus, Ohio; & JP-A-60 202 810 (Nichiban Co., Ltd) Oct. 14, 1985.
Chemical Abstracts, vol. 94, 1981, p. 366, resume No. 180497q, Columbus, Ohio; & JP-A-81 16407 (Nitto Electric Industrial Co., LT) Feb. 17, 1981.

Primary Examiner—Thurman K. Page
Assistant Examiner—William E. Benston, Jr.
Attorney, Agent, or Firm—Pollock, Vande Sande & Priddy

[57] ABSTRACT

A disposable depilatory composition including an elastomer, a resin and a softener or sweetener. This composition can be deposited on the skin in a thin layer and can be stripped from the skin without use of a film such as cellophane.

20 Claims, No Drawings

DEPILATORY COMPOSITION

This application is a continuation of Ser. No. 07/348,621 filed PCT/FR88/00328 on Jun. 21, 1988, now abandoned.

The present invention relates to a new depilatory composition, its mode of preparation and its use.

BACKGROUND OF THE INVENTION

At the present time, compositions generally called "waxes" are used for depilation purposes, based on resins either pure or modified, mixed with fat products such as: bees-wax, mineral wax, oil, lanolin, etc . . .

These compositions are applied on the skin in the hot state as a relatively thick layer, and are reusable after filtration. The thickness of the layer allows the wax not to cool down too rapidly and therefore to retain a certain degree of flexibility, since below a certain temperature (25°/30°), the wax becomes completely hard and brittle and is therefore unusable in that state.

One uses also other compositions, generally called lukewarm waxes, based on resin or modified resin, or on a synthetic resin, fat products, and other products such as glucose, honey, etc.

This type of wax called a disposable wax, is applied in a thin layer and is removed with the assistance of a cellulose material strip, notably a "cellophane" band or a nonwoven, film.

On the other hand, the present applicant has proposed (see European patent number 86 400 311 published under number 0 194 181) a new depilatory composition, called "low temperature" and "disposable", meaning that it is not intended to be reused after filtration, with its main constituent being a resin salt, and notably a triethanolamine resinate, which is also applied in a very thin layer and is removed with the assistance of a strip of cellulose film, and notably of "cellophane".

SUMMARY OF THE INVENTION

The present invention aims at providing a new generation of depilatory compositions, more easily used than the depilatory compositions presently available.

To this effect, the invention relates to a new depilatory composition or "depilatory wax" of the "low temperature" and "disposable" type, characterized by the fact that:

1) it contains a main constituent an elastomeric and/or thermoplastic macro-molecular compound, allowing a control of the resiliency of the composition at room temperature and without this wax breaking into pieces due to the homogeneity imparted to the mixture;

2) there is added to this main constituent:

a natural or modified resin imparting tackniness to the product;

softeners and sweeteners such as, for example, fats (lanolin, talloil), natural or synthetic waxes (bees-wax, paraffin, micro-crystalline wax, etc.), oils (colzaseed oil, litmus oil, corn oil, vaseline oil, etc.) and possibly fillers (calcium carbonate or titanium dioxide), whereby this depilatory wax can be deposited in a thin layer, in contrast to hot waxes which are deposited in a relatively thick layer, or to the so-called disposable lukewarm waxes which have to be used with a strip of "cellophane".

Amongst the elastomers which can be used as an essential constituent of the depilatory composition according to the present invention, one may cite notably (of course this list having by no way any limiting character):

natural rubber, and synthetic elastomers chosen notably in the groups including:

the copolymers or terpolymers of ethylene-propylene;

the styrene-butadiene copolymers;

the vinyl ethylene-acetate copolymers;

the acrylic polymers;

the butadiene, isoprene, isoprene-isobutene, isobutene, chloroprene elastomers;

the nitrile rubbers;

the polyester thermoplastic elastomers.

According to a preferred but not limiting way of providing a depilatory wax according to the invention, said wax has the following composition:

| | |
|---|---|
| Elastomer | 5 to 15% by weight |
| Resin and modified resin | 40 to 80% by weight |
| Softener (wax or oil) | 10 to 20% by weight |

The composition can also include fillers such as notably calcium carbonate or titanium dioxide in a proportion of the order of 5 to 15%.

According to the invention, the hereabove depilatory composition, once it has been previously slightly heated, becomes an unctuous liquid of which a small quantity is taken by using a spatula so as to apply it in the direction of the hairs in the form of strips having dimensions varying according to the part to be depilated. These strips have the property of being applied in a thin and regular layer on the skin.

One can also apply the wax by using a distributing apparatus, heated or not, and provided with a tank adapted to contain wax. The compound is left on the skin for a few moments to "set" so that the thin layer gives rise, through lymerization, to a thin plastic film which catches the hairs without adhering to the skin, since the strip has lost its tackiness, in its outer surface on top and underneath. Thereafter, it is enough to peel away the thin film in order to pull out the hairs captured in the band.

It is possible, by replacing in the hereabove mentioned formula the resins by some types of liquid resins, to use the depilatory product according to the invention at room temperature without having to previously heat it. However, this product has to be kept sheltered from the air when stored.

The following example is given without any limiting character a mode of preparation of a depilatory composition according to the present invention.

One begins by melting the chosen elastomer at a temperature between 90° and 160° C., as a function of the nature of said elastomer. There is then added to the product thus obtained all the other hereabove mentioned components, while maintaining the temperature of the mixture at a minimum of more or less 100° C. Since the elastomer is not a soluble product, it is necessary to provide a depilatory product of great homogeneity to mix it for a certain duration in an appropriate stirrer.

Of course, this invention is not limited to the hereabove described embodiments and it encompasses all the variants thereof.

I claim:

1. A disposable depilatory composition which can be applied in liquid form on the surface of the skin and which is removable by peeling away from the surface of the skin after setting to a thin plastic layer and losing its tackiness, said composition consisting essentially of:
- an elastomeric compound in the amount of about 5 to 15% by weight;
- a resinous material in the amount of about 40 to 80% by weight;
- a softener in the amount of about 10 to 20% by weight; and, wherein the relative amounts of said elastomeric compound, said resinous material and said softener are such that said composition upon setting through polymerization to a thin plastic film is capable of catching hairs without adhering to the skin and being removable by peeling away from the skin along with the hairs caught in the thin plastic film.

2. A depilatory composition according to claim 1 wherein said elastomeric compound is natural rubber.

3. A depilatory composition according to claim 1 wherein said elastomeric compound is a synthetic elastomer selected from the group consisting of:
- ethylene-propylene copolymers;
- ethylene-propylene terpolymers;
- styrene-butadiene copolymers;
- vinyl ethylene-acetate copolymers;
- acrylic polymers;
- butadiene, isoprene, isoprene-isobutene, isobutene and chloroprene elastomers;
- nitrile rubbers; and,
- polyester thermoplastic elastomers.

4. A depilatory composition according to claim 1 wherein said resinous material is a natural resin.

5. A depilatory composition according to claim 1 wherein said resinous material is a modified resin.

6. A depilatory composition according to claim 1 wherein said softener is selected from the group consisting of a fat, an oil and a wax.

7. A disposable depilatory composition which can be applied in liquid form on the surface of the skin and which is removable by peeling away from the surface of the skin after setting to a thin plastic layer and losing its tackiness, said composition consisting essentially of:
- an elastomeric compound in the amount of about 5 to 15% by weight;
- a resinous material in the amount of about 40 to 80% by weight;
- a softener in the amount of about 10 to 20% by weight;
- a filler selected from the group consisting of calcium carbonate and titanium dioxide in an amount of about 5 to 15% by weight; and wherein the relative amounts of said elastomeric compound, said resinous material and said softener are such that said composition upon setting through polymerization to a thin plastic film is capable of catching hairs without adhering to the skin and being removable by peeling away from the skin along with the hairs caught in the thin plastic film.

8. A depilatory composition according to claim 7 wherein said elastomeric compound is natural rubber.

9. A depilatory composition according to claim 7 wherein said elastomeric compound is a synthetic elastomer selected from the group consisting of:
- ethylene-propylene copolymers;
- ethylene-propylene terpolymers;
- styrene-butadiene copolymers;
- vinyl ethylene-acetate copolymers;
- acrylic polymers;
- butadiene, isoprene, isoprene-isobutene, isobutene and chloroprene elastomers;
- nitrile rubbers; and
- polyester thermoplastic elastomers.

10. A depilatory composition according to claim 7 wherein said resinous material is a natural resin.

11. A depilatory composition according to claim 7 wherein said resinous material is a modified resin.

12. A depilatory composition according to claim 7 wherein said softener is selected from the group consisting of a fat, an oil and a wax.

13. A method for removing hair which comprises applying to the surface of skin containing hair to be removed a disposable depilatory composition consisting essentially of:
- an elastomeric compound in the amount of about 5 to 15% by weight;
- a resinous material in the amount of about 40 to 80% by weight;
- a softener in the amount of about 10 to 20% by weight; and wherein the relative amounts of said elastomeric compound, said resinous material and said softener are such that said composition upon setting to a thin plastic film is capable of catching hairs without adhering to the skin and being removable by peeling away from the skin along with the hairs caught in the thin plastic film;
- permitting said composition to set to a thin plastic film to thereby catch hairs without adhering to the skin; and
- removing said thin plastic film by peeling away from the skin along with the hairs caught in said plastic film.

14. A method according to claim 13 wherein said elastomeric compound is natural rubber.

15. A method according to claim 13 wherein said elastomeric compound is a synthetic elastomer selected from the group consisting of:
- ethylene-propylene copolymers;
- ethylene-propylene terpolymers;
- styrene-butadiene copolymers;
- vinyl ethylene-acetate copolymers;
- acrylic polymers;
- butadiene, isoprene, isoprene-isobutene, isobutene and chloroprene elastomers;
- nitrile rubbers; and
- polyester thermoplastic elastomers.

16. A method according to claim 13 wherein said composition includes a filler selected from the group consisting of calcium carbonate and titanium dioxide in an amount of about 5 to 15% by weight.

17. A method according to claim 13 wherein said resinous material is a natural resin.

18. A method according to claim 13 wherein said resinous material is a modified resin.

19. A method according to claim 13 wherein said softener is selected from the group consisting of a fat, an oil and a wax.

20. The method according to claim 13 which further comprises heating aid composition prior to applying it to the surface of skin.

* * * * *